United States Patent
Ruchala et al.

(10) Patent No.: US 6,915,005 B1
(45) Date of Patent: Jul. 5, 2005

(54) METHOD FOR RECONSTRUCTION OF LIMITED DATA IMAGES USING FUSION-ALIGNED REPROJECTION AND NORMAL-ERROR-ALIGNED REPROJECTION

(75) Inventors: Kenneth J. Ruchala, Madison, WI (US); Gustavo H. Olivera, Verona, WI (US); Thomas R. Mackie, Verona, WI (US); Jeffrey M. Kapatoes, Madison, WI (US); Paul J. Reckwerdt, Madison, WI (US)

(73) Assignee: Tomo Therapy Incorporated, Madison, WI (US)

( * ) Notice: Subject to any disclaimer, the term of this patent is extended or adjusted under 35 U.S.C. 154(b) by 0 days.

(21) Appl. No.: 10/170,252

(22) Filed: Jun. 11, 2002

Related U.S. Application Data

(63) Continuation-in-part of application No. 09/802,468, filed on Mar. 9, 2001.

(51) Int. Cl.[7] .............................. G06K 9/00; G06K 9/46; G06K 9/40; G06K 9/36; G06K 9/32
(52) U.S. Cl. ....................... 382/131; 382/132; 382/190; 382/275; 382/284; 382/294
(58) Field of Search ................................. 382/131, 132, 382/294, 190, 275, 284; 250/363.03; 378/901; 600/407

(56) References Cited

U.S. PATENT DOCUMENTS

| | | |
|---|---|---|
| 5,317,616 A | 5/1994 | Swerdloff et al. |
| 5,351,280 A | 9/1994 | Swerdloff et al. |
| 5,394,452 A | 2/1995 | Swerdloff et al. |
| 5,442,675 A | 8/1995 | Swerdloff et al. |
| 5,528,650 A | 6/1996 | Swerdloff et al. |
| 5,548,627 A | 8/1996 | Swerdloff et al. |
| 5,552,605 A * | 9/1996 | Arata .......................... 378/901 |

(Continued)

OTHER PUBLICATIONS

Maes, F., "Multimodality Image Registration by Maximization of Mutual Inforamtion", IEEE Transactions on Medical Imaging, Apr. 1997.

Viola, P., "Alignment by Maximization of Mutual Information", Fifth International Conference on Computer Vision, Jun. 1995.

(Continued)

*Primary Examiner*—Mehrdad Dastouri
(74) *Attorney, Agent, or Firm*—Godfrey & Kahn, S.C.

(57) ABSTRACT

The present invention provides methods of using current but incomplete data to prepare an approximated complete image of a patient potentially undergoing radiation therapy. A complete image of the patient is fused or aligned with a limited patient image using image registration techniques. The aligned image is converted to sinogram data. This sinogram data is compared to sinogram data corresponding to the limited patient image to determine what data exists beyond the scope of the limited sinogram. Any additional data is added to the limited data sinogram to obtain a complete sinogram. This complete sinogram is then reconstructed into an image that approximates the complete image that would have been taken at the time the limited image was obtained.

33 Claims, 14 Drawing Sheets

U.S. PATENT DOCUMENTS

| | | | | |
|---|---|---|---|---|
| 5,579,358 A | * | 11/1996 | Lin | 378/901 |
| 5,625,190 A | * | 4/1997 | Crandall | 250/363.03 |
| 5,625,663 A | | 4/1997 | Swerdloff et al. | |
| 5,647,663 A | | 7/1997 | Holmes | |
| 5,661,773 A | | 8/1997 | Swerdloff et al. | |
| 5,673,300 A | | 9/1997 | Reckwerdt et al. | |
| 5,724,400 A | | 3/1998 | Swerdloff et al. | |
| 5,761,331 A | * | 6/1998 | Clark, III | 382/131 |
| 5,800,353 A | * | 9/1998 | McLaurin, Jr. | 600/407 |
| 5,907,594 A | | 5/1999 | Lai | |
| 5,954,650 A | * | 9/1999 | Saito et al. | 382/128 |
| 5,961,454 A | * | 10/1999 | Kooy et al. | 600/407 |
| 6,009,212 A | * | 12/1999 | Miller et al. | 382/131 |
| 6,167,296 A | * | 12/2000 | Shahidi | 600/427 |
| 6,266,453 B1 | * | 7/2001 | Hibbard et al. | 382/131 |
| 6,324,243 B1 | * | 11/2001 | Edic et al. | 378/901 |
| 6,618,467 B1 | * | 9/2003 | Ruchala et al. | 378/65 |

OTHER PUBLICATIONS

Van Den Elsen, P.A., "Automatic registration of CT and MR Brain Images Using Correlation of Geometrical Features", IEEE Transactions on Medical Imaging, Jun. 1995.

Web Site information: www.intouchlive.com/journals/oncology/09910sup5s.htm; 3D Treatment Planning and Intensity–Modulated Radiation Therapy.

Web Site information: www.phoenix5.org/Infolink/Michalski/; Three–Dimensional Conformal Radiation Therapy (3dcrt) for Prostate Cancer.

Web Site information: www.oncolink.com/templates/treatment/article.cfm?c=5&s=33&id=182; Intensity Modulated Radiation Therapy; An Introduction for Patients and Clinicians.

* cited by examiner

METHOD FOR RECONSTRUCTION OF LIMITED DATA IMAGES USING FUSION-ALIGNED REPROJECTION AND NORMAL-ERROR-ALIGNED REPROJECTION

CROSS-REFERENCE TO RELATED APPLICATIONS

This application is a continuation in part of U.S. application Ser. No. 09/802,468, filed Mar. 9, 2001, entitled "System and Method for Fusion-Aligned Reprojection of Incomplete Data," the disclosure of which is incorporated herein by reference.

BACKGROUND OF THE INVENTION

The present invention relates generally to radiation therapy equipment for the treatment of tumors, and more particularly to methods for reconstructing incomplete patient data for radiation therapy and treatment verification.

Medical equipment for radiation therapy treats tumorous tissue with high energy radiation. The amount of radiation and its placement must be accurately controlled to ensure both that the tumor receives sufficient radiation to be destroyed, and that the damage to the surrounding and adjacent non-tumorous tissue is minimized.

External source radiation therapy uses a radiation source that is external to the patient to treat internal tumors. The external source is normally collimated to direct a beam only to the tumorous site. Typically, the tumor will be treated from multiple angles with the intensity and shape of the beam adjusted appropriately. The source of high energy radiation may be x-rays or electrons from a linear accelerator in the range of 2–25 MeV, or gamma rays from a highly focused radioisotope such as $Co^{60}$ source having an energy of 1.25 MeV.

One form of external radiation therapy uses the precision of a computed tomography (CT) scanner to irradiate cancerous tissue in addition to acquiring CT images immediately before, immediately after, and/or during radiation treatment delivery. It is particularly useful to have online CT imaging capability integrated into a radiotherapy delivery system since it helps identify changes in a patient's position and anatomy between the time of imaging and treatment. However, many current patient imaging systems, especially ones that are integrated into radiotherapy treatment systems suffer from a limited field-of-view (LFOV) in that collected imaging data does not encompass the patient's complete cross-section. This LFOV can cause visibility problems with the images, images with artifacts, images with distorted values, and affect applications that use these images, including dose calculations, delivery verification, deformable patient registration, deformable dose registration, contouring (automatic, manual, or template-based).

Intensity modulated radiation therapy uses intensity modulated radiation beams that enter the patient's body at a greater number of angles and positions than conventional therapies, thereby lessening the amount of radiation that healthy tissues are subjected to and concentrating the radiation where it is needed most, at the cancer site(s). Essentially, the radiation field is "sculpted" to match the shape of the cancerous tissue and to keep the dose of radiation to healthy tissue near the cancer low. This type of radiotherapy greatly benefits from visualization of a patient's internal anatomy and accurate calculation of the delivered radiation dose. A radiation treatment plan may be based on a CT image of the patient. As is known in the art, a CT image is produced by a mathematical reconstruction of many projection images obtained at different angles about the patient. In a typical CT image, the projections are one-dimensional line profiles indicating the attenuation of the beam by a "slice" of the patient. The actual CT data is held in sinogram space as a matrix wherein each row represents a gantry position, a gantry angle, a ray angle or the like (a first sinogram dimension); each column represents a detector number, a detector distance, a detector angle, a ray position, or the like (a second sinogram dimension). A third sinogram dimension is commonly used with multi-row or volumetric detectors, representing each detector row. The matrix of data obtained in a CT image can be displayed as a sinogram 10 as shown in FIG. 1, or reconstructed into a two-dimensional image 12, as shown in FIG. 2.

In some radiotherapy systems, a physician views the cancerous areas on a CT image and determines the beam angles and intensities (identified with respect to the tumor image) which will be used to treat the tumor. In an automated system, such as that disclosed in U.S. Pat. No. 5,661,773, the disclosure of which is hereby incorporated by reference, a computer program selects the beam angles and intensities after the physician identifies the tumorous region and upper and lower dose limits for the treatment.

More specifically, planning CT images are used to create a three-dimensional (3-D) treatment plan of a region of interest. This region of interest is broken down into units called voxels, which are defined as volumetric pixels. Each voxel is then assigned a particular radiation dose depending on what type of tissue or other matter it contains, e.g. cancerous tissue, healthy tissue, air, water, etc.

Normally, the planning CT image of a patient is acquired substantially before the radiation treatment to allow time for the treatment plan to be prepared. However, the position of organs or other tissue to be treated can change from day-to-day because of a variety of factors. Further, patients move during treatment because of breathing, muscle twitching, or the like, and many patients are larger than the field-of-view (FOV) of the online CT imaging system. Uncertainty in the positioning of the patient with respect to the planning CT image can undermine the conformality of the radiation delivery.

Thus, it is highly preferable to verify the treatment plan based on data obtained just prior to the time of treatment. This verification process can be done by techniques that compare the planning image to an image of the patient at the time of treatment. Acquisition of an online tomographic image for the latter provides the benefits of 3-D tomographic imaging without requiring that the patient move between the imaging and treatment steps.

Unfortunately, the imaging data sets obtained on the day of treatment to be used for preparing the patient model are often incomplete or limited. These limitations may be caused by limited FOVs set by the field size of the multi-leaf collimator (MLC) attached to the linear accelerator and the detector size of the radiotherapy system. The limitations may also be caused by patients that are too large to fit within the FOV of the CT imaging system associated with the radiotherapy equipment applying the radiation dose, yielding a LFOV image as shown in FIG. 3, which shows only a portion of the image shown in FIG. 2. The FOV or image data sets may also be intentionally limited by modulated treatment data or region-of-interest tomography (ROIT) involving reconstruction of treatment data, intentionally only delivered to a specific region(s). For example, in FIG. 3, not only is there a LFOV, but the data around the edges contains significant artifacts so that the image has an irregular border and internal values that are distorted.

As mentioned above, the LFOV of radiotherapy images creates problems of impaired visibility and degraded dose calculations. The most common reasons for impaired visibility are the limited field size of the MLC attached to the linear accelerator and the limited detector size. These limitations prevent the CT imaging system from collecting complete FOV data for all sizes of patients at all sites. The problem of degraded dose calculations is caused by distorted electron densities and the loss of peripheral information for attenuation and scatter from the LFOV images. This distortion of image values and loss of peripheral information can likewise affect other applications that utilize these images.

To resolve the problem of limited imaging data sets in which only a portion of an image is obtained, several scans of the patient may be made at various detector or patient positions, and then combined into a complete set. This has been done by adding together sinogram data, but requires that the imaging apparatus or patient position can be reliably modified accordingly. This is often not possible. Further, the problem of artifacts is still present due to the significant degree of mismatch between such data sets, while the additional handling of the patient is more costly, time intensive and can be difficult for frail patients. Moreover, patients receiving multiple scans receive higher doses of radiation than with a single scan.

Reconstruction of incomplete imaging data sets using available techniques results in images that do not show the complete extent of the patient's body, can have artifacts and incorrect voxel values, and thus, limit the extent to which the images can be used for applications including delivery verification, dose reconstruction, patient set-up, contouring, deformable patient registration and deformable dose registration. Accordingly, a need exists for methods that can solve problems caused by limited imaging data sets.

SUMMARY OF THE INVENTION

The present invention relates to methods by which an incomplete CT patient data set can be combined with an existing CT patient data set to create an image of a patient that is complete and with fewer artifacts. The present invention provides methods for utilizing complete planning CT data for reconstruction of incomplete CT data with particular regard for a patient's daily anatomical variations. The complete planning CT data is used as prior information to estimate the missing data for improving and reconstructing incomplete CT patient data.

In a first embodiment of the present invention, the method includes the steps of obtaining first and second sinogram data sets or images from a patient. Both data sets are converted to images, and aligned together so that statistically, there is optimal registration between the two images. The aligned or "fused" image is reprojected as a sinogram. This reprojected sinogram is compared to either the first or second sinogram to determine what data exists beyond the scope of the first or second sinogram. This additional data is added to the sinogram to which the reprojected sinogram was compared to obtain an augmented sinogram The augmented sinogram is then converted or reconstructed to an image, referred to as a fusion-aligned reprojection (FAR) image.

The method of the first embodiment of the present invention is advantageous in that the availability of only one limited data sinogram/image will not affect the ability to perform accurate delivery verification, dose reconstruction, patient setup or the like. The previously taken complete image or "second image" is fused, or aligned, to the limited data image or "first image." The sinogram representing the fused image is compared to the limited data sinogram, and the augmented limited data sinogram is prepared therefrom. From the augmented limited data sinogram the FAR image is obtained. The FAR image is used to accurately apply radiation to the treatment area, which may be positioned differently or contain anatomical changes as compared to the previously obtained complete image.

FAR compensates for limited data radiotherapy images by enhancing the conspicuity of structures in treatment images, improving electron density values, and estimating a complete representation of the patient. FAR combines the LFOV data with prior information about the patient including CT images used for planning the radiotherapy. The method of the first embodiment includes aligning or "fusing" the LFOV image and the planning image, converting the images into "sinogram space", merging the images in sinogram space, and reconstructing the images from sinograms into normal images. A key step of the FAR method is "fusion" or alignment of the planning image with the LFOV image. However, if a patient's treatment position is close to the planning position, explicit fusion under the FAR method may not be necessary. Instead, an implicit fusion may be adequate if the normal setup error is sufficiently small.

Under these circumstances when this implementation of FAR is not viable or necessary, it is possible to replace the explicit fusion of FAR with an implicit fusion, referred to as normal-error-aligned reprojection (NEAR). NEAR, another embodiment of the present invention, is a variation of FAR for situations where explicit fusion is not possible or does not yield good results. Specifically, NEAR is accomplished when the images are already sufficiently aligned, as often results from using common radiotherapy patient setup protocols. The patient is often positioned within a few millimeters and a few degrees of the intended position, creating a normal setup error which constitutes the implicit fusion of NEAR.

A benefit of NEAR is that it may enable an iterative (two or more) variation of FAR (NEAR2FAR). It is possible to iterate these methods using multiple applications of FAR, or going from NEAR to FAR (NEAR2FAR) for a two-iteration process. NEAR can be followed by FAR iterations, or FAR can be tried multiple times with different registration results. After creating a NEAR image, the quantitatively improved voxel values in the FOV might enable an explicit fusion with the planning image, and a FAR image could be generated. NEAR and NEAR2FAR may be particularly beneficial when a LFOV causes severe quantitative and qualitative degradation of the images, whether because of a large patient, a small detector or MLC, or because a ROIT strategy is being pursued. NEAR may also be quicker than FAR, as no time is required to do an explicit fusion.

NEAR, FAR, and NEAR2FAR utilize planning CT data or other images as imperfect prior information to reduce artifacts and quantitatively improve images. These benefits can also increase the accuracy of dose calculations and be used for augmenting CT images (e.g. megavoltage CT) acquired at different energies than planning CT images.

FAR, NEAR and NEAR2FAR may also be used for multi-modality imaging (combining CT images with MRI images, etc.). While an MRI image may have different image values, they may be correctable, or they may show the patient boundary, which might be enough.

The methods of the present invention improve the data by aligning the LFOV and planning images, and merging the data sets in sinogram space, or vice versa. One alignment option is explicit fusion, for producing FAR images. For cases where explicit fusion is not viable, FAR can be implemented using the implicit fusion of NEAR. The optional iterative use of NEAR and/or FAR is also possible, as are applications of NEAR and FAR to dose calculations and the compensation of LFOV online megavoltage CT images with kilovoltage CT planning images as mentioned above.

Various other features, objects, and advantages of the invention will be made apparent to those skilled in the art from the following detailed description, claims, and accompanying drawings.

DETAILED DESCRIPTION OF THE INVENTION

Figure 1:
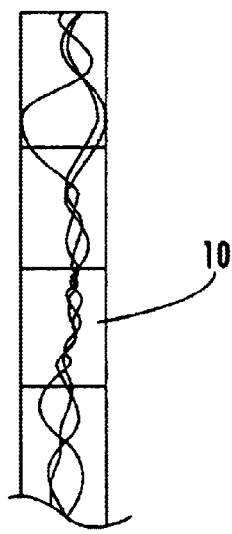
FIG. 1 an example of a sinogram obtained from the CT image of a patient.
Figure 2:
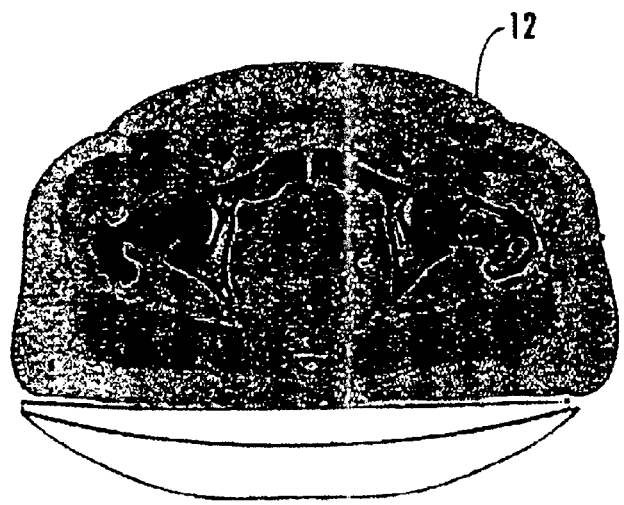
FIG. 2 is an example of a planning image of a patient obtained from a sinogram similar to that shown in FIG. 1.

Referring now to the drawings, FIG. 1 is an example of a sinogram 10 obtained from the CT image of a patient. FIG. 2 is an example of a planning CT image obtained from a sinogram similar to that shown in FIG. 1, and FIG. 3 is an example of a LFOV image from an online CT scan of the patient just prior to radiotherapy treatment.

Figure 3:
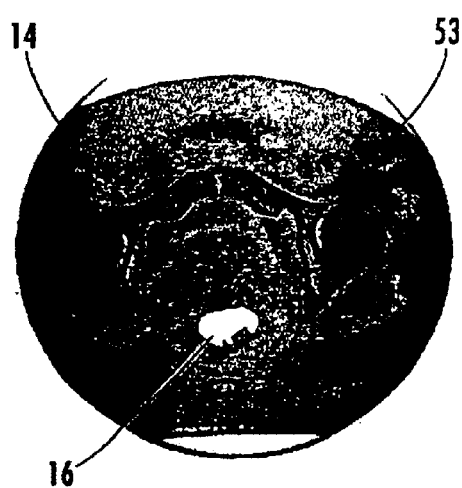
FIG. 3 is an example of a LFOV treatment image of a patient.
Figure 4:
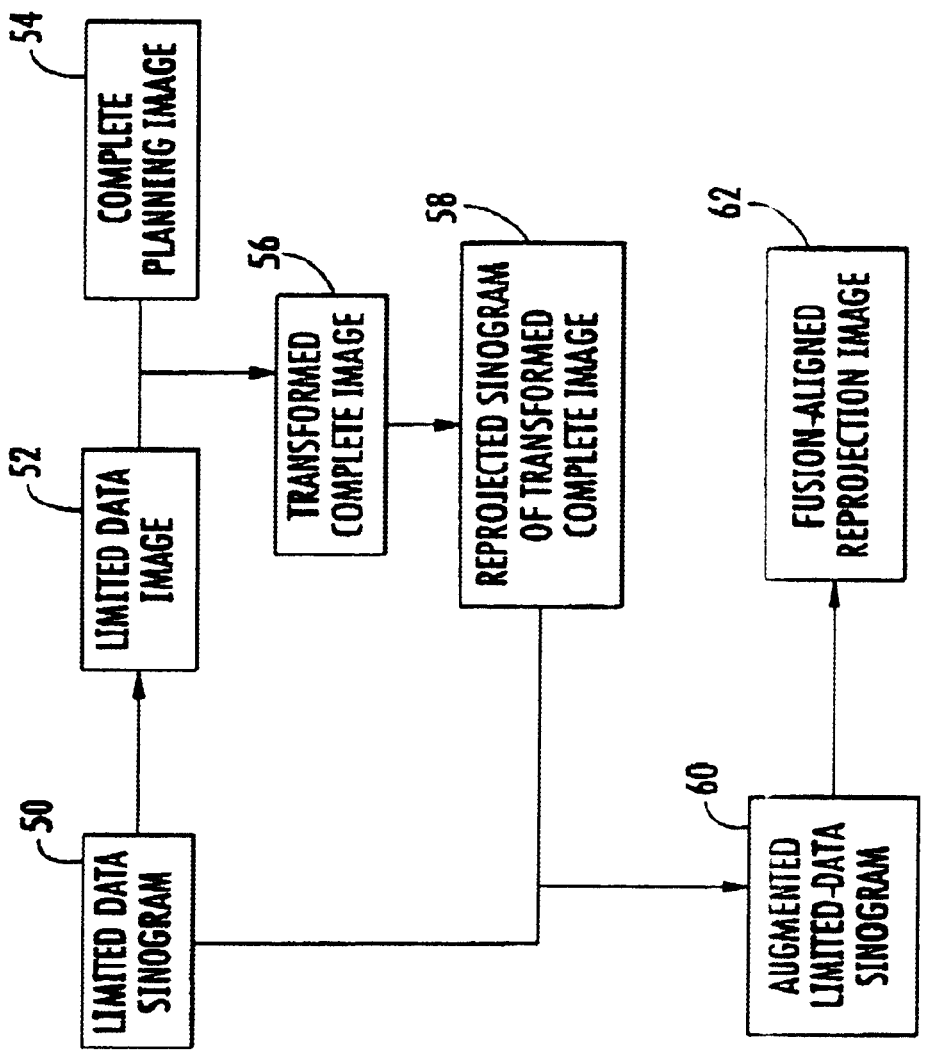
FIG. 4 is a flow diagram showing the steps involved in creating a FAR treatment image in accordance with a first embodiment of the present invention.

A preferred method in accordance with a first embodiment of the present invention is shown in the flow diagram of FIG. 4. FIG. 4 represents the first embodiment process involved in creating a fusion-aligned reprojection (FAR) image from a limited data image and a complete planning image. The process begins by obtaining a limited data sinogram 50 typically representing the treatment area from a patient. The limited data sinogram 50 is preferably obtained near the time that the patient is receiving his or her radiation treatment, but may be obtained at any time. The limited data sinogram 50 is reconstructed to a limited data image 52, as seen in the examples of FIGS. 1 and 3, and represented schematically in FIG. 6 as limited object 156. FIG. 3 contains a significant amount of artifacts such as a white irregular border 53 around the image along with some image distortion of image values. By way of example, the treatment area targeted in FIG. 3 is of a prostate. However, the methods of the present invention can be applied to images of any part of the body, or be used in other applications, such as veterinary medicine or extended to industrial uses.

Figure 5:
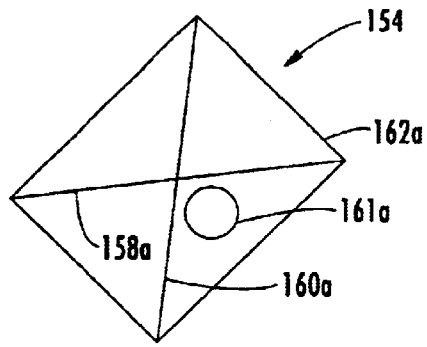
FIG. 5 is a schematic representation of a full image scan of a patient.

A complete planning image 54 of the same patient and same treatment area, as shown by way of example in FIG. 2 as image 12, and represented schematically in FIG. 5 as object 154, is typically obtained prior to obtaining the limited data image 52, image 14 of FIG. 3, for the purpose of treatment planning. Even if limited data image 52, image 14 of FIG. 3, were taken only minutes after the complete planning image 54, image 12 of FIG. 2, there are often inherent differences between the location of certain organs and/or tissue due to motion caused by normal bodily functions as the patient travels from the planning CT system to the treatment system and is setup again. Additionally, if enough time has elapsed between images, weight loss or growth of certain tissue can also occur. Internal organ motion also causes some degradation relative to planned dose distribution.

It is noted that complete planning image 54, image 12 of FIG. 2, or limited data image 52, image 14 of FIG. 3, need not be from a CT scanner or imager, and that this technique can be generally applied to matching images from different projection imaging or multi-modality imaging, such as magnetic resonance imaging (MRI), positron emission tomography (PET), or single photon emission computed tomography (SPECT). Where different imaging types are used, there may be misalignment or disagreement between images values due to the differing methods of data collection. In addition, cross-energy compensation of LFOV online megavoltage CT images with kilovoltage CT planning images is also contemplated in the various embodiments of the present invention.

Figure 6:
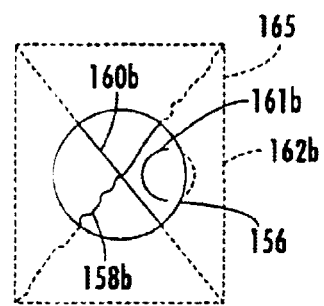
FIG. 6 is a schematic representation of FIG. 5 with illustrative "anatomical" changes and a different alignment, a limited image portion is shown in the center, and the remaining portion, which was not fully scanned, is shown in phantom.

The two images 12 and 14 shown in FIGS. 2 and 3 and represented schematically in FIGS. 5 and 6 by objects 154 and 156, have differences between them. In the actual image examples of FIGS. 2 and 3, intestinal gas 16 is shown in FIG. 3, thereby displacing the treatment target. In the schematic example of FIGS. 5 and 6, object 154 is composed of diagonals 158a and 160a and an inclusion 161a, within a frame 162a. Limited object 156 shows only corresponding diagonals 160b and 158b, and part of the inclusion designated as 161b. Thus, there is a change between diagonal 158a and 158b and only partial data for inclusion 161b.

Figure 7:
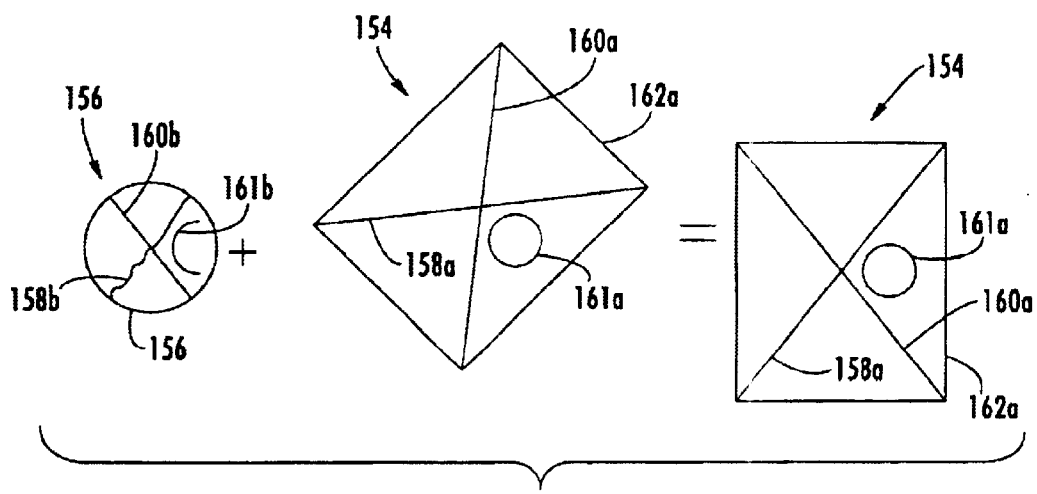
FIG. 7 demonstrates how the full image of FIG. 5 is aligned to the limited image of FIG. 6 as used to achieve the resulting FAR image.
Figure 10:
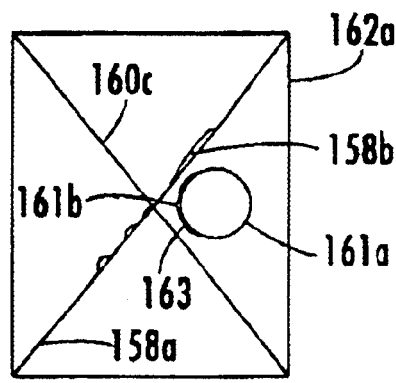
FIG. 10 shows a schematic representation of the actual alignment or "fusion" of the images of FIGS. 5 and 6.

As shown in FIG. 4, "fusion" or image registration techniques are used to align limited data image 52 and complete image 54. In the schematic example in FIG. 7, limited object 156 is fused with complete object 154 so that statistically, there is optimal registration between the objects 154 and 156. FIG. 7 shows how the orientation of object 154 is aligned to closely match that of object 156. FIG. 10 shows diagonal 160c as the perfect registration between diagonals 160a and 160b. There is less than perfect registration between diagonals 158a and 158b. Both lines are superimposed only by way of example to show that fusion is not perfect as evidenced by the double edge 163. To the contrary, a theoretically perfect fusion may not exist in the context of anatomical changes, and is not a requirement for these methods.

FAR is not specific to the registration technique. It could be through automatic, manual, or hybrid methods that are known in the art. Image registration or fusion may be achieved by several techniques. One such technique is known as mutual information (MI), for which a well-known algorithm has been developed. One such example of this algorithm being used to register multi-modal images is described in the following publication, incorporated herein by reference: Frederik Maes, Andre Collignon, Dirk Vendermeulen, Guy Marchal, and Paul Suetens, *Multimodality Image Registration by Maximization of Mutual Information*, Vol. 16, No. 2, IEEE Transactions on Medical Imaging, 187 (April 1997).

Extracted Feature Fusion (EFF) is another registration technique providing numerous advantages over prior art techniques. EFF is a voxel-based image registration method, wherein only extracted features of images are registered or fused. For example, a patient's bone structure usually stays the same even when a patient loses a substantial amount of weight. Therefore, the bones can in effect be extracted from each image subject to alignment, and then registered using statistical methods. In the simple example of FIG. 5, diagonal 160a and frame 162 may represent bone or tissue that remains relatively unchanged over time. Therefore, only these relatively static features might be selected for fusion, while other features that are more dynamic, perhaps diagonals 158a, 158b and inclusion 161a, 161b, need not be included in the registration calculations.

The benefits of registering only an extracted portion of an image are reduced calculation times, improved accuracy, and more clearly defined goals for alignment in cases where the patient has significantly changed in shape. The speed benefits arise from the registration of fewer data points, which in this case are voxels. The total processing time is generally proportional to the number of points selected, so reducing that number from the size of the entire three-dimensional image set to a subset of points meeting certain criteria (e.g. voxels that represent bone or do not represent air) will typically reduce calculation times. This reduction of voxels can provide more accurate results than other methods of reducing the number of voxels for MI techniques, such as regular down-sampling.

Other image registration techniques include manual fusion, alignment using geometric features (e.g., surfaces), gradient methods, and voxel-similarity techniques. Sinogram-based registration techniques could also be applied.

Any useful LFOV registration for FAR, whether automatic, manual or hybrid, implies that there is some information in those images in spite of any quantitative and qualitative degradation. In these cases, the goal of FAR is to quantitatively and qualitatively improve upon the information present by incorporating additional prior information. Yet, as FOV's become more severely reduced, images may lose their utility for automatic fusion, manual fusion and visual inspection. There are also a number of other reasons why automatic fusion may not provide the desired result, such as finding a local minimum. Another problem with fusion is that in the presence of anatomical changes there may not be an unambiguous correct alignment, as some structures may align well at the expense of others, as demonstrated in FIG. 10. In these cases, NEAR, iterative application, and testing multiple registrations provide additional opportunities.

Referring again to FIG. 4, the aligned or transformed complete image 56 is reprojected as a sinogram 58. The data for sinogram 58 is once again in a matrix wherein each row represents an angle, and each column represents a distance. The data matrix of the reprojected sinogram 58 is compared to the data matrix for limited data sinogram 50 to determine what data is missing from the limited data sinogram 50. This is now possible because the reprojected sinogram of the transformed complete image 58 is in alignment with the limited data sinogram 50.

Figure 8:
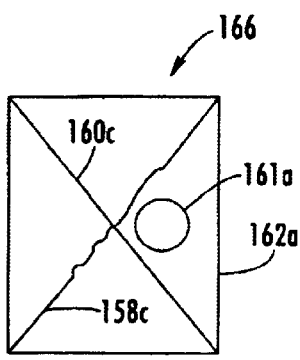
FIG. 8 is a schematic representation of a FAR image.
Figure 9:
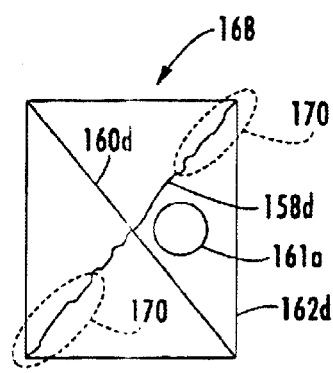
FIG. 9 is a schematic representation of a full image corresponding to the image of FIG. 6.

The approximation of the missing sinogram data from the reprojected sinogram of transformed complete image 58 is added to the limited data sinogram 50 to create an augmented limited data sinogram 60. The augmented limited data sinogram 60 is reconstructed to a FAR image 62 that is an approximation of what the complete image would have looked like at the time the limited data image 52 was obtained. The FAR image 62 is represented schematically in FIG. 8. Frame 162a is the same as in FIG. 5, and diagonals 158c, 160c and inclusion 161c are now complete. This can compared to the object 168 in FIG. 9, which represents the image that would have been taken at the time of treatment if it were possible to obtain a complete image. The fact that the outer regions 170 of diagonal 158d are not the same as diagonal 158c is not critical to the invention.

Figure 11:
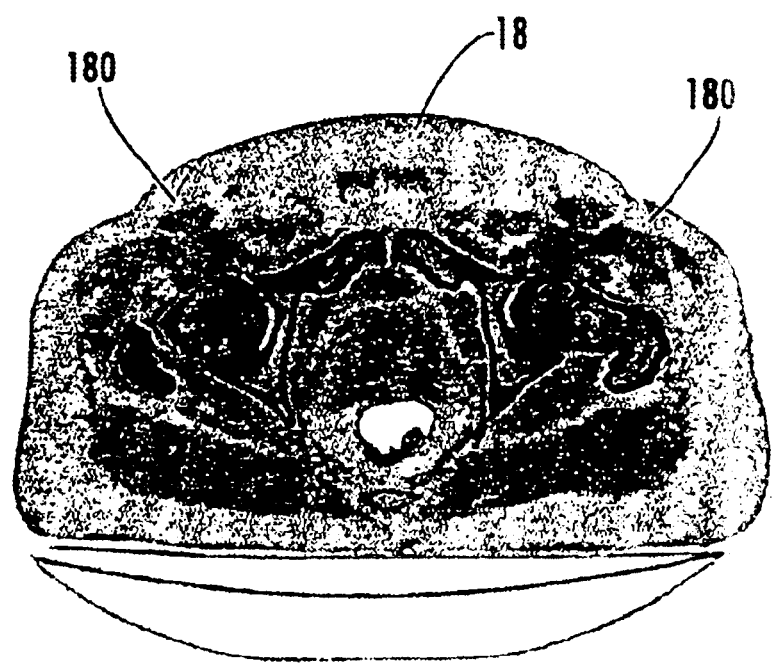
FIG. 11 is a reconstructed FAR image of FIGS. 2 and 3 aligned in accordance with the method of the present invention.

FIG. 11 represents a reconstructed FAR image obtained by combining the sinograms of the LFOV and the complete planning images shown in FIGS. 2 and 3 in accordance with the method of a first embodiment of the present invention. It can be seen that slight artifacts such as the faint ring 180 as shown in FIG. 11 can still result from this method. However, such artifacts are insignificant because they do not impair the conspicuity of the important structures in the FOV, nor are they noticeably detrimental to dose calculations or other processes that utilize these images.

The reconstructed FAR image obtained from the method of the first embodiment of the present invention can then be used for patient setup (positioning the patient prior to delivery), contouring (identifying target regions and sensitive structures, either automatically, manually, or with a template-based approach), dose registration (changing delivery patterns to compensate for patient position and/or tumor changes), delivery verification (using a signal measured at an exit detector to compute energy fluence directed toward a patient), deformable patient registration and deformable dose registration (using anatomical, biomechanical and region of interest data to map changes in the patient's anatomy between each fraction, a reconstructed dose is mapped to a reference image to obtain a cumulative dose).

Figure 12:
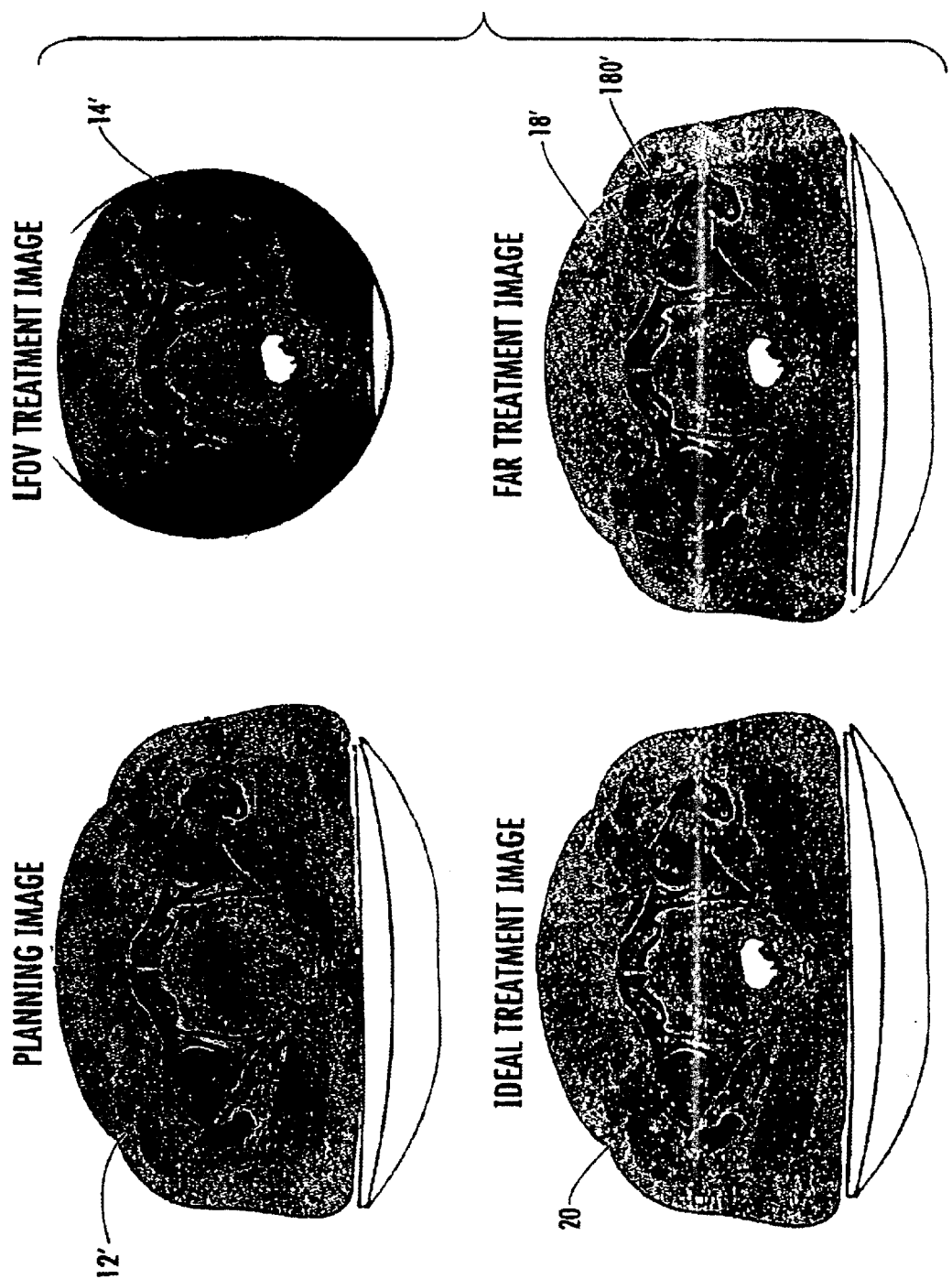
FIG. 12 shows a comparison of a planning image, a LFOV treatment image, an ideal treatment image, and a FAR treatment image.

FIG. 12 shows the comparison of a planning image 12', which is equivalent to the planning CT image 12 of FIG. 2, a LFOV treatment image 14', which is equivalent to the LFOV image 14 of FIG. 3, an ideal treatment image 20, and a FAR treatment image 18', which is equivalent to the FAR image 18 of FIG. 11. It should be noted that the FAR treatment image 18 and 18' is substantially similar to the ideal treatment image 20, except for the slight artifact rings 180 and 180' that do not impair the conspicuity of the important structures in the FOV, nor are they noticeably detrimental to dose calculations.

Figure 13:
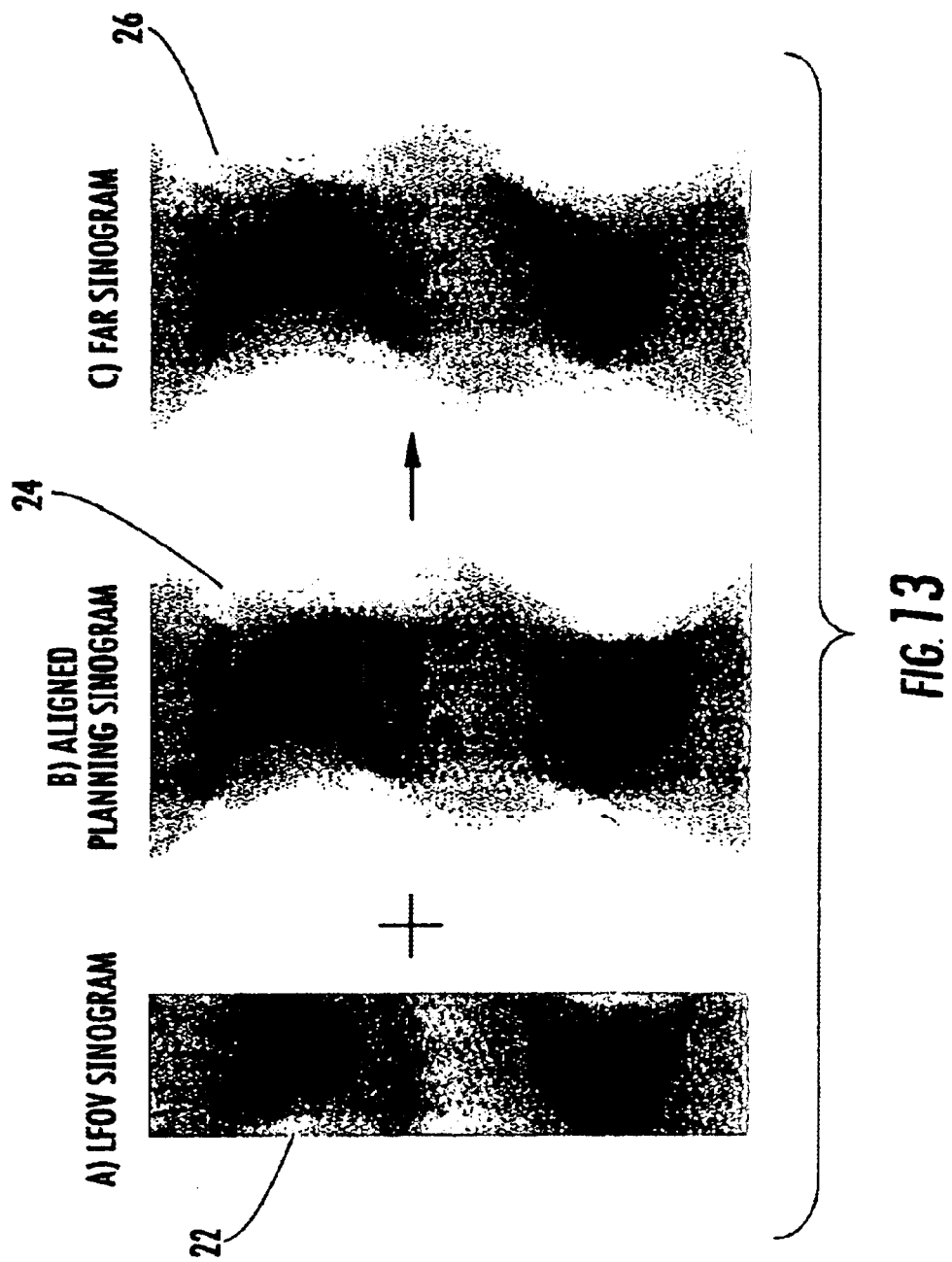
FIG. 13 shows an example FAR sinogram obtained by merging a LFOV online sinogram and an aligned planning CT sinogram.

The completion process of FIG. 4 can be seen in sinogram space in FIG. 13. FIG. 13 shows an example FAR sinogram 26 obtained by merging a LFOV sinogram 22 with an aligned planning sinogram 24. The truncated limited data sinogram 22 is shown in FIG. 13A. The missing data from the LFOV sinogram 22 is estimated from the aligned planning sinogram 24 shown in FIG. 13B. The resulting FAR sinogram 26 shown in FIG. 13C estimates the missing data from the aligned planning sinogram 24 of FIG. 13B.

Figure 14:
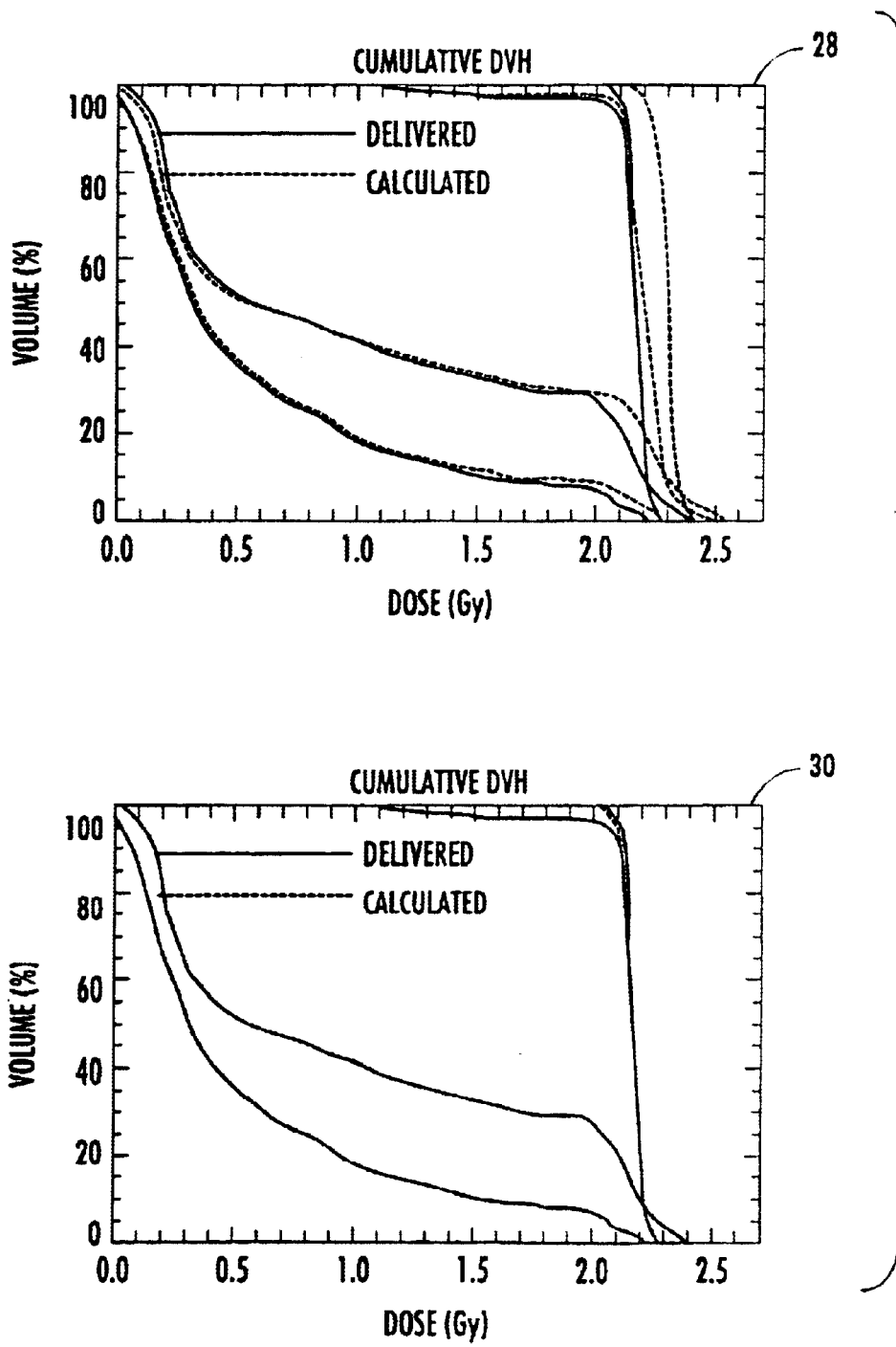
FIG. 14 shows a comparison of radiotherapy dose calculations for a LFOV image and a FAR image.

FIG. 14 shows a comparison of radiotherapy dose calculations for a LFOV image 28 and a FAR image 30. The LFOV image 28 results in substantial dose calculation errors, while the FAR image 30 yields near perfect dose calculations. The LFOV dose volume histogram 28 (DVH) shows both overestimation and underestimation between the calculated and delivered doses, while the FAR DVH 30 shows that the doses calculated and delivered for the FAR image are near perfect. The DVHs calculated with FAR images are virtually identical to those for the complete images.

Figure 15A:
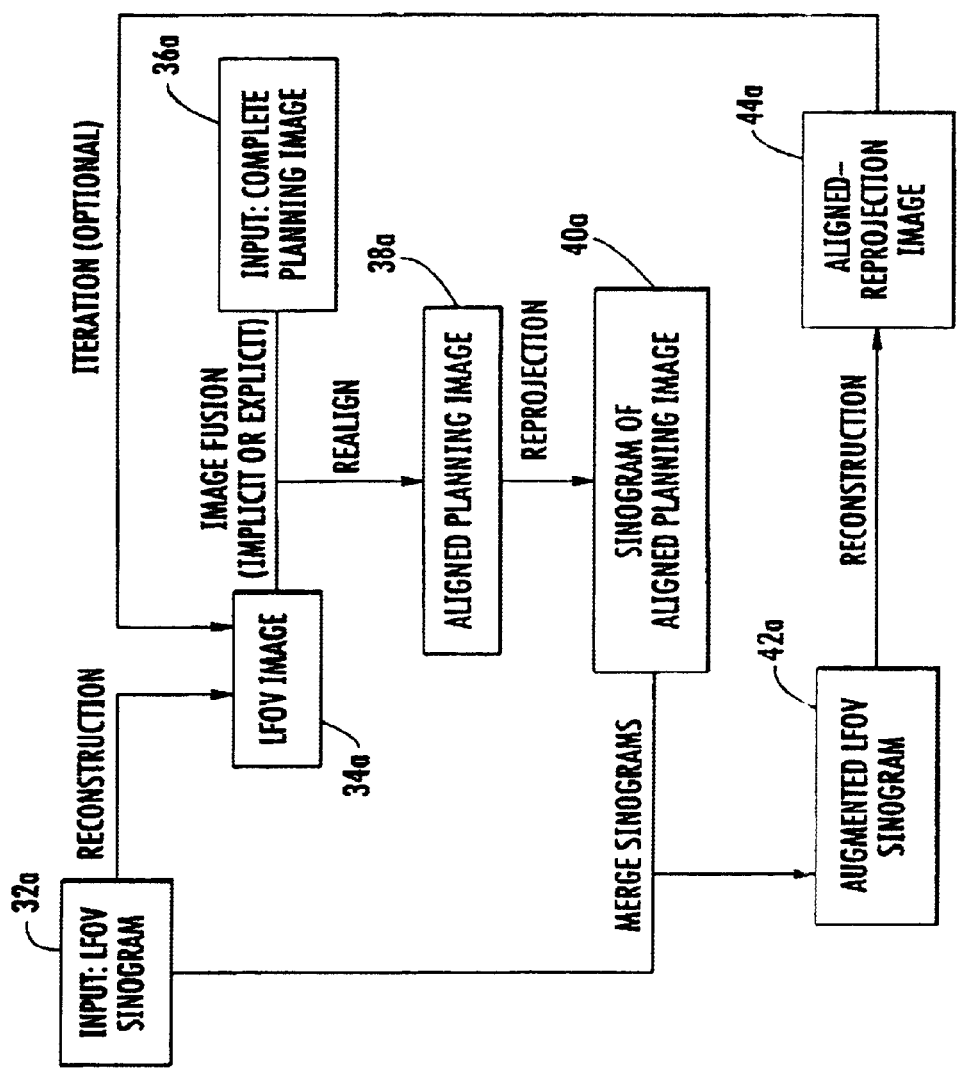
FIG. 15A is a flow diagram showing the steps involved in creating an aligned reprojection image in accordance with the present invention.
Figure 15B:
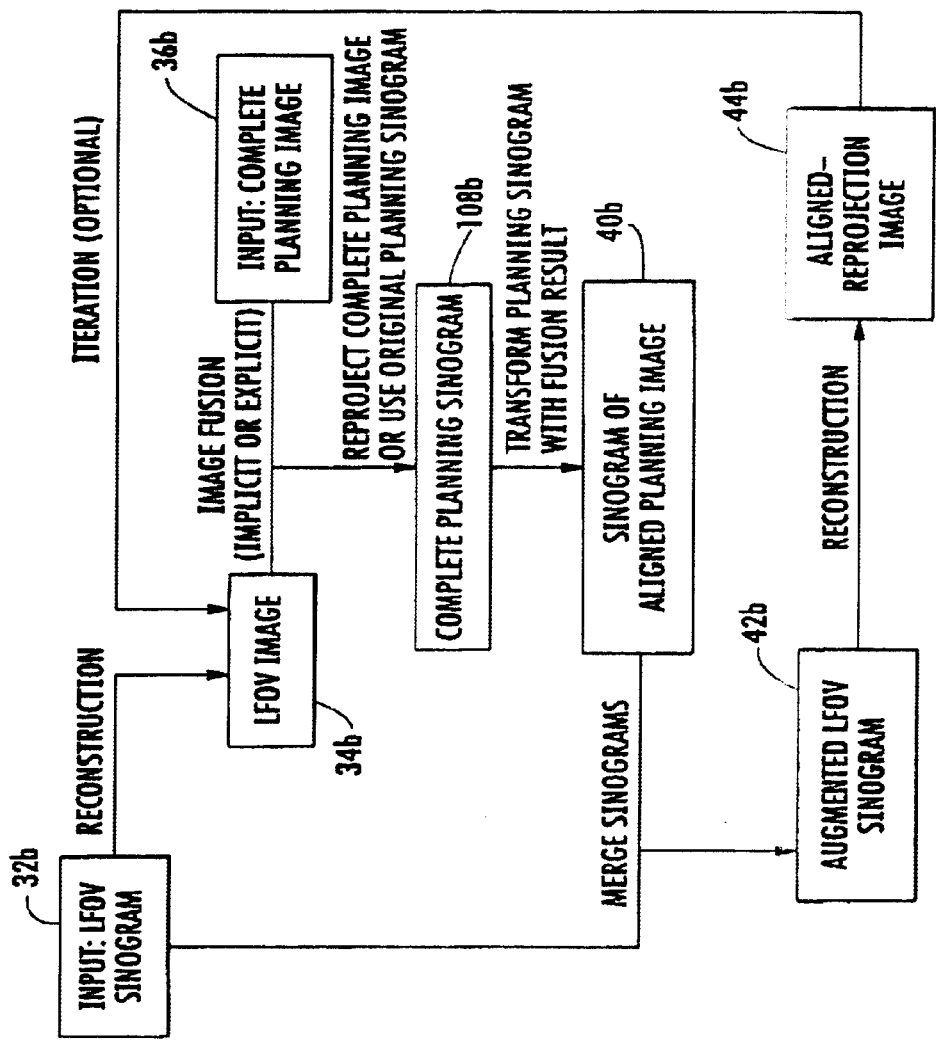
FIG. 15B is a flow diagram showing the steps involved in creating an aligned reprojection image in accordance with a different embodiment of the present invention.
Figure 15C:
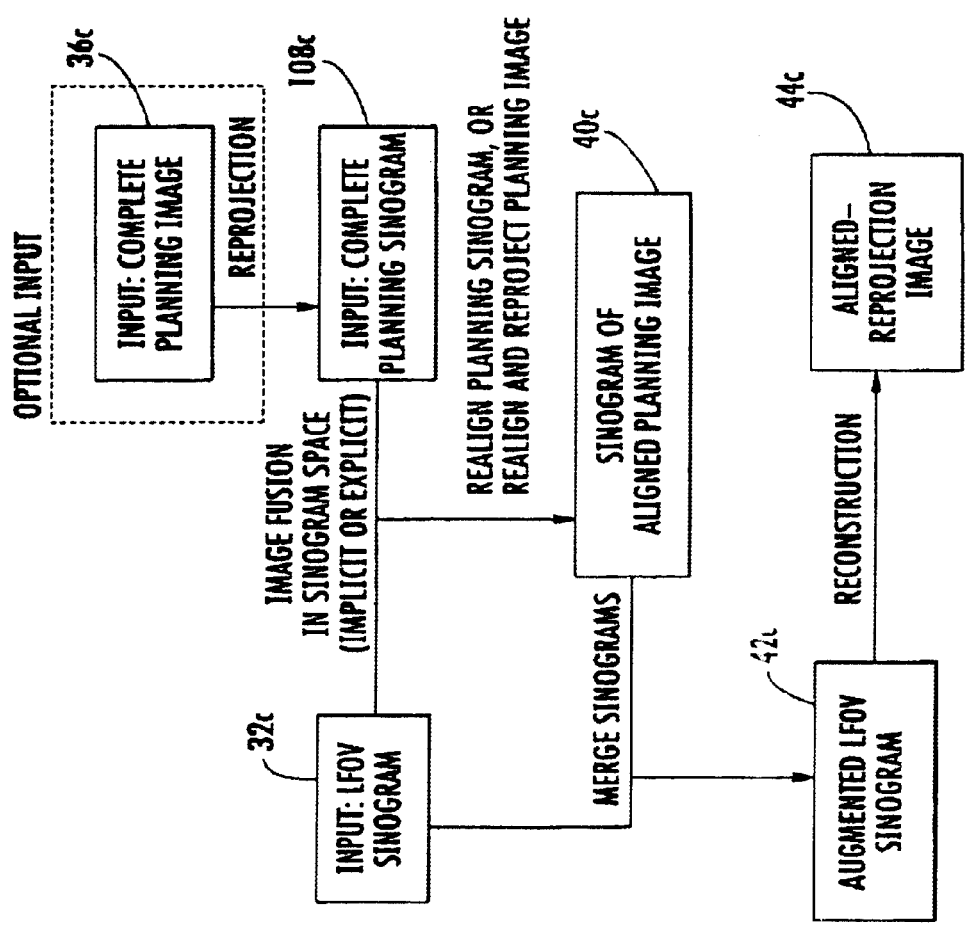
FIG. 15C is a flow diagram showing the steps involved in creating an aligned reprojection image in accordance with another different embodiment of the present invention.

FIGS. 15A, 15B, and 15C represent different embodiments of methods involved in creating an aligned-reprojection image from a limited data image or sinogram and a complete planning image or sinogram. Referring first to FIG. 15A, a FAR, NEAR, or NEAR2FAR image is created by obtaining a limited data sinogram 32A representing the treatment area from a patient. The limited data sinogram is reconstructed to a limited data image 34A. A complete planning image 36A of the same patient is typically obtained prior to obtaining the limited data image 34A. Image fusion or image registration techniques are used to align the complete planning image 36A with the limited data image 34A. The aligned complete planning image 38A is reprojected as a sinogram 40A. The reprojected sinogram of the aligned planning image 40A is compared to the limited data sinogram 32A. The missing sinogram data from the reprojected sinogram 40A is added or merged with the limited data sinogram 32A to create an augmented limited data sinogram 42A. The augmented limited data sinogram 42A is reconstructed to an aligned-reprojection image 44A that is an approximation of what the complete image would have looked like at the time the limited data image was obtained. The aligned-reprojection image may be fed back to the limited data image 34A for a multiple iteration method to possibly achieve better results. The above method is flexible with regard to which image (e.g., complete FOV planning image or limited online FOV image) is realigned to the other and reprojected. What matters is that the complete planning image is used to estimate the missing data from the limited data image. For example, the complete planning image could be realigned to the LFOV image creating an aligned planning image, reproject the aligned planning image to a sinogram, augment or merge the LFOV sinogram with the aligned planning sinogram to yield an augmented LFOV sinogram, and reconstruct the augmented LFOV sinogram to an aligned-reprojection image as shown in FIG. 15A. Or alternatively, the LFOV image could be realigned to the complete planning image creating an aligned LFOV image, reproject the aligned LFOV image to a sinogram, augment that sinogram with the complete planning sinogram to yield an augmented LFOV sinogram, and reconstruct the augmented LFOV sinogram to an aligned-reprojection image.

The method of realigning the image and reprojecting it into a sinogram can be mathematically streamlined as shown in FIGS. 15B and 15C. Generally, the relative alignment between the complete planning image and the limited data image is determined. Then, instead of realigning the complete planning image to the limited data image and reprojecting the aligned planning image to a sinogram, one can realign the complete planning sinogram to the limited data sinogram (or vice versa), which is an alternate, but equivalent, method of achieving the same result; a realigned sinogram of the planning image. The aligned planning sinogram is then used to estimate the missing data from the limited data sinogram which is augmented into the limited data sinogram. The augmented limited data sinogram is then reconstructed to create an aligned-reprojection image.

This alternate embodiment allows an estimate of the missing data from a limited data sinogram with an aligned complete planning sinogram. It does not matter conceptually how the sinogram is realigned, whether an image is realigned and reprojected or if the sinogram is realigned directly.

FIG. 15B illustrates another embodiment of a method for creating an aligned-reprojection image from a limited data sinogram or image and a complete planning image or sinogram. The inputs to the process are a complete planning image 36B or complete planning sinogram 108B and a LFOV sinogram 32B. The LFOV sinogram 32B is initially reconstructed into a LFOV image 34B and then fused (explicit (FAR) or implicit (NEAR)) with the complete planning image 36B. The complete planning image 36B is reprojected to a sinogram or the original planning sinogram 108B is transformed with the fusion result to yield an aligned planning image 40B. The sinogram data of the aligned planning image 40B is used to estimate the data missing from the LFOV sinogram 32B. The limited data sinogram 32B is merged with the aligned planning image sinogram 40B, resulting in an augmented limited data sinogram 42B. This augmented limited data sinogram 42B is reconstructed into an aligned-reprojection image 44B. The aligned-reprojection image may supersede the original limited data image 34B for a multiple iteration process (NEAR2FAR).

FIG. 15C illustrates yet another embodiment of the present invention for creating an aligned-reprojection image from a limited data sinogram and a complete planning image or sinogram. The inputs to the process are a limited data sinogram 32C and either an optional complete planning image 36C or most preferably a complete planning sinogram 108C. If the process starts with a complete planning image 36C as one of the inputs, then that image is reprojected to sinogram space to yield a complete planning sinogram 108C. The limited sinogram 32C is fused in sinogram space (explicit (FAR) or implicit (NEAR)) with the complete planning sinogram 108C. The next step involves realigning the complete planning sinogram 108C, or realigning and reprojecting the complete planning image 36C using the same fusion result. The resulting aligned planning image sinogram 40C is merged with the limited data sinogram 32C to create an augmented limited data sinogram 42C. The augmented limited data sinogram 42C is then reconstructed into an aligned-reprojection image 44B.

To summarize the differences between the alternate embodiment methods of FIG. 15C, the fusions are performed in sinogram-space as the limited data sinogram 32C is fused (implicit or explicit) to the complete data sinogram 108C, unlike the embodiments of FIGS. 15A and 15B that use image fusion. Based upon the sinogram fusion, the realigned planning sinogram 40C can be created by realigning sinogram 108C, or by realigning planning image 36C and reprojecting into sinogram space. The process is then the same for each case. The aligned planning sinogram 40C is merged with the limited data sinogram 32C to create an augmented limited data sinogram 42C. The augmented limited data sinogram 42C is then reconstructed into an aligned-reprojection image 44B.

Figure 16:
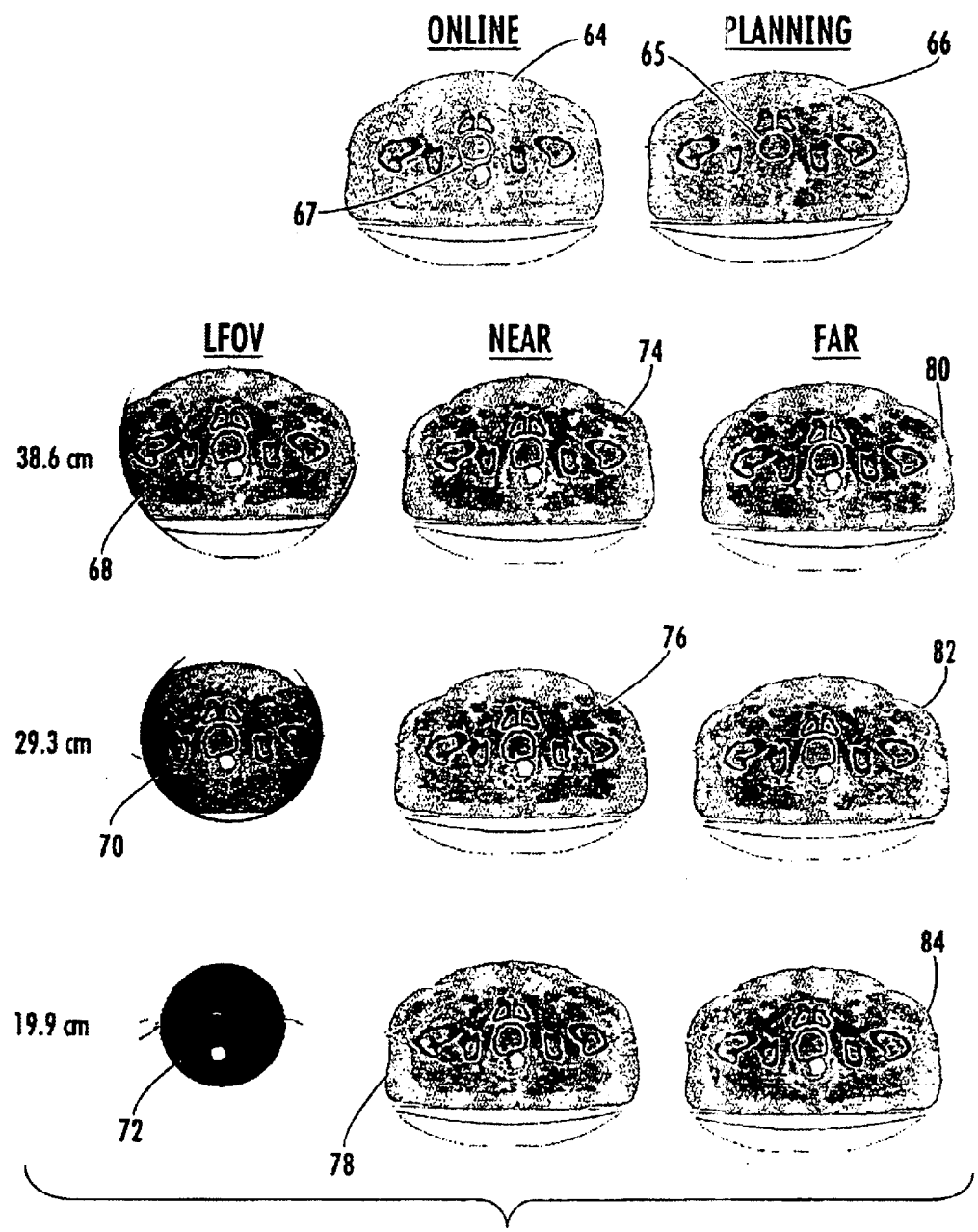
FIG. 16 shows examples of LFOV images, NEAR images, and FAR images for field-of-view sizes of 38.6, 29.3, and 19.9 cm based upon the online image.

FIG. 16 shows representative images from a planning CT image 66 and the corresponding online image 64. The contours 65 for the planning images are shown in black, while the contours 67 for the online images are shown in white. Three different LFOV images 68, 70, 72, NEAR images 74, 76, 78, and FAR images 80, 82, 84 for field-of-view sizes of 38.6, 29.3, and 19.9 cm are shown based upon the online image 64. As the FOV decreases, the artifacts become more severe in the LFOV images 68, 70, 72, while the NEAR 74, 76, 78 and FAR images 80, 82, 84 are less affected. These images are representative of how NEAR and FAR can utilize available information to qualitatively improve the reconstructions for a range of FOV sizes. In this particular case, there is little visual difference between the NEAR and FAR images. The similarity of NEAR and FAR images can occur for several reasons. Where the normal setup error is small, the explicit fusion will generally not improve much upon the normal error, or because the anatomical differences between the planning CT image 66 and the online image 64 are a more significant factor than the alignment between those images, there will also be little improvement.

NEAR and FAR can utilize available information to qualitatively improve the reconstructions for a range of FOV sizes. The explicit and implicit fusion align the planning data with the LFOV data. A LFOV online image augmented with NEAR or FAR can produce images that are quantitatively closer to the complete FOV online image than the planning image alone. NEAR and FAR create quantitative improvements and artifact reductions, and also improve upon the accuracy of dose calculations. FAR may not be possible if the distortion of image values preclude a successful fusion. In this case, a NEAR image is created, and by fusing or aligning the NEAR image to the planning CT image, a NEAR2FAR image is generated, further reducing artifacts and improving alignment. The results of an iterative application of NEAR and FAR are shown in FIG. 17.

Figure 17:
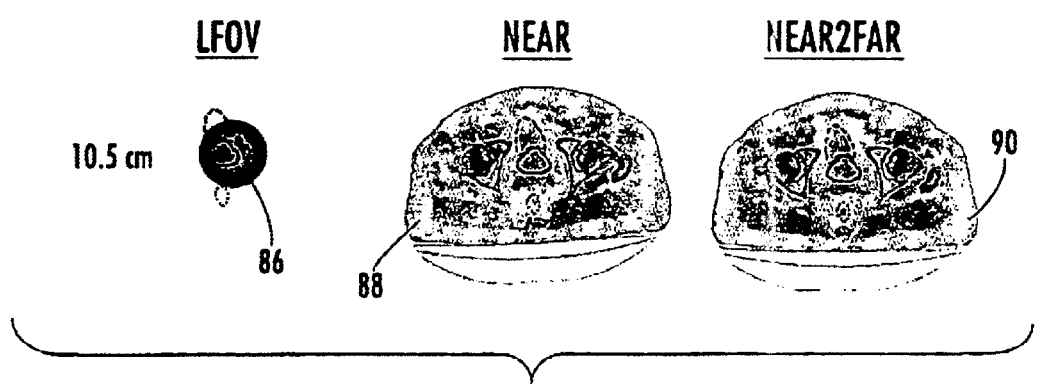
FIG. 17 shows a LFOV reconstruction for a 10.5 cm FOV, a NEAR reconstruction, and a two iteration NEAR2FAR reconstruction.

FIG. 17 shows a LFOV reconstruction 86 for a 10.5 cm FOV, a NEAR reconstruction 88, and a two iteration NEAR2FAR reconstruction 90. In this case, a FAR reconstruction was not immediately possible because the distortion of image values precluded a successful fusion. A NEAR image was created, and by fusing the interior scan region to the planning CT image, a two iteration NEAR2FAR image could be generated.

Figure 18:
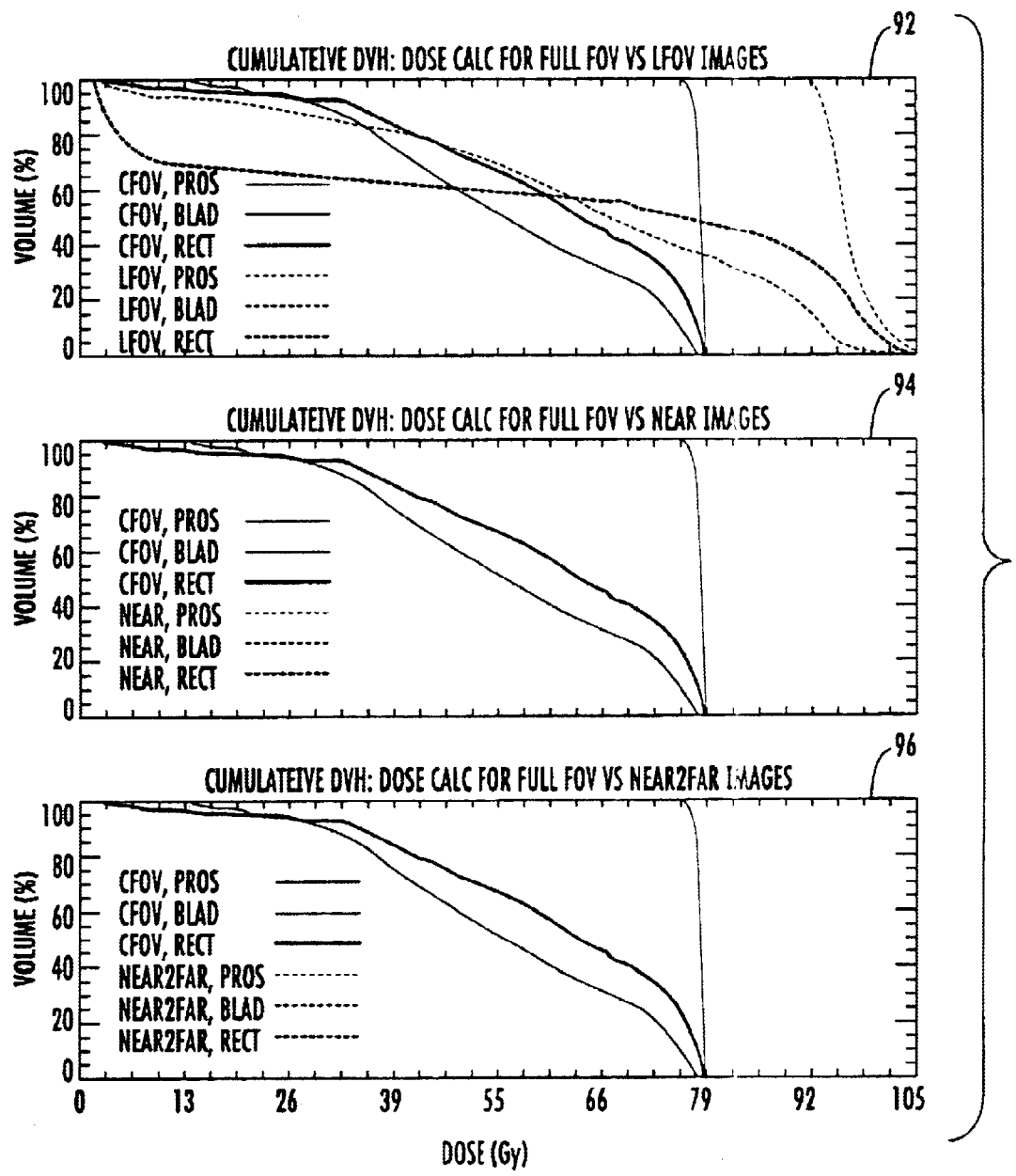
FIG. 18 shows a comparison of radiotherapy dose calculations for complete FOV online images and a LFOV image, a NEAR image, and a NEAR2FAR image, for rectal points, bladder points, and prostate points.

FIG. 18 shows a comparison of radiotherapy dose calculations for complete FOV online images and a LFOV image 92, a NEAR image 94, and a NEAR2FAR image 96, for prostate points, bladder points, and rectal points. The DVH's (Dose Volume Histogram) are based upon the known contours from the complete FOV online image. The LFOV dose calculation overestimates the prostate dose by approximately 15%, and the rectum and bladder doses have areas of both overestimation and underestimation. The dose distributions calculated using NEAR and NEAR2FAR produce DVH's indistinguishable from the full FOV dose calculation.

Figure 19:
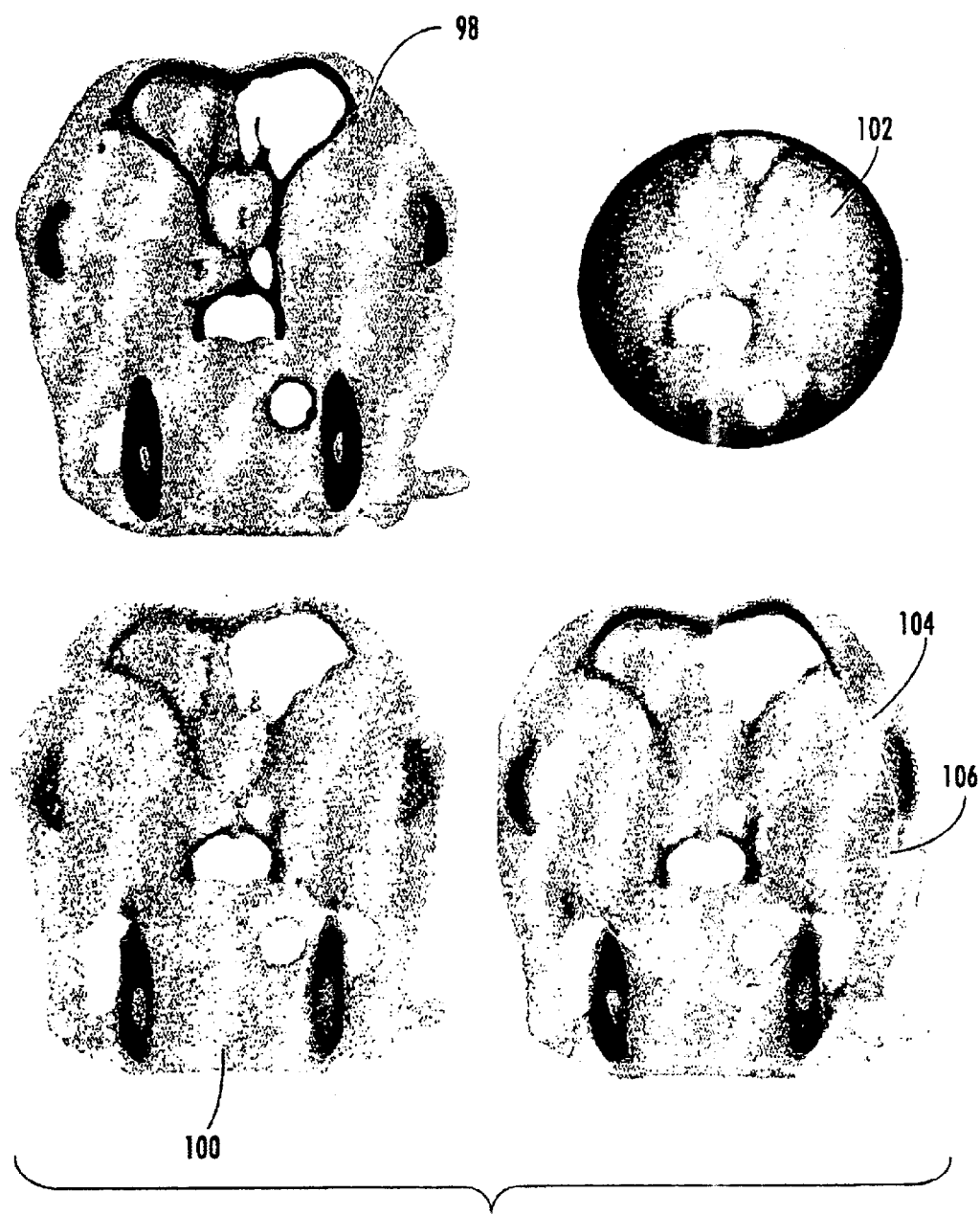
FIG. 19 shows canine CT images from a kilovoltage CT scanner, a megavoltage CT scanner, a LFOV version of the megavoltage image, and a FAR reconstruction from the LFOV data augmented with planning CT data.

FIG. 19 shows canine CT images from a kilovoltage CT scanner 98, a megavoltage CT scanner 100, a LFOV version of the megavoltage image 102, and a FAR reconstruction 104 from the LFOV data augmented with planning CT data. Of particular interest is that these data sets were not only acquired on different CT systems but at different energies, requiring that FAR combine megavoltage and kilovoltage data. The resulting FAR image 104 includes slight artifacts 106 that can result from this method. However, such artifacts 106 are insignificant because they do not impair the conspicuity of the important structures in the FOV, nor are they noticeably detrimental to dose calculations or other processes that utilize these images.

As discussed above, the methods of the present invention may be used for purposes beyond radiotherapy in cases where potentially imperfect prior information is available. While the present description has primarily disclosed use of prior information in the form of a planning CT, it is feasible to apply NEAR and FAR to multi-modality images, such as creating a FAR image by combining an online CT (megavoltage or kilovoltage) data set with a planning MRI image. In such cases, the MRI or other-modality image needs to be converted to values compatible with the LFOV data set. A complex mapping of values will provide the best results, but even using the alternate modality image to describe the patient's outer contour and using a water-equivalency assumption will provide benefits. This is particularly true considering the demonstrated robustness of FAR with regard to anatomical changes, imperfect alignments, and even systematic differences in reconstructed values between megavoltage and kilovoltage CT images. As described above, FAR can also combine megavoltage and kilovoltage CT data. In FIG. 19, FAR was used to augment megavoltage CT data sets with kilovoltage planning CT data sets.

Other applications include using NEAR and FAR for dose calculations, iterative application of NEAR and FAR for severely limited FOV's, FIG. 17, and using FAR for a combination of kilovoltage and megavoltage CT images, FIG. 19. Dose calculations are typically based upon CT images and require reconstructed values that can be calibrated to electron densities. The artifacts and quantitative distortions introduced by FOV truncations may degrade this calibration, while the lack of peripheral information can impair the scatter and attenuation calculations often performed when computing dose.

The methods described above for the present invention can be applied regardless of the reason(s) the image data set is limited. This includes hardware constraints, such as FOV's set by MLC size or detector size, etc. The methods may also be applied to intentionally limited data sets or FOV's. An example of this is called region-of-interest tomography (ROIT), in which the scan FOV is intentionally limited to reduce patient dose, even though complete FOV data sets are available. A particular example would be reconstruction of treatment data, intentionally only delivered to a specific region(s) of the body. This delivery would constitute a partial CT sinogram, and FAR or NEAR could estimate the missing data. More generally, the limited data is not necessarily LFOV, but can also be more complex patterns of missing data, such as modulated treatment data. NEAR and FAR may also be extensible to other types of limited data situations, such as limited slice or limited-projection images.

While the invention has been described with reference to preferred embodiments, it is to be understood that the invention is not intended to be limited to the specific embodiments set forth above. It is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

We claim:

1. A method of augmenting a tomographic projection image of a patient, the method comprising the steps of:
   obtaining a first sinogram data set from a patient;
   reconstructing the first sinogram data set into a first image;
   obtaining a second sinogram data set from the patient;
   reconstructing the second sinogram data set into a second image;
   aligning the first image to the second image to obtain an aligned image, so that optimal registration between the first and second image is obtained;
   reprojecting the aligned image into a reprojected sinogram data set;
   extracting data from the reprojected sinogram data set that is not available in the first sinogram data set;
   augmenting the first sinogram data set with the extracted data from the reprojected sinogram data set to obtain an augmented sinogram data set; and
   reconstructing the augmented sinogram data set into a third image.

2. The method according to claim 1 wherein the first sinogram data set contains limited data.

3. The method according to claim 2 wherein the limited data sinogram data set, the reprojected sinogram data set and the augmented limited data sinogram data set are represented by a data matrix, wherein each row represents a gantry position, a gantry angle, or a ray angle; each column represents a detector number, a detector distance, a detector angle, or a ray position; and a third sinogram dimension may optionally represent multiple detector rows.

4. The method according to claim 1 wherein the second image contains complete data.

5. The method according to claim 4 wherein the limited data image is realigned to the complete data image, reprojected, and its missing data is augmented with data from the complete data sinogram data set.

6. The method according to claim 1 wherein the second image contains limited data, but is less-limited or limited in a different manner than the first sinogram data set such that the first sinogram data set can be augmented from a second sinogram data set or the reprojected sinogram data set.

7. The method according to claim 1 wherein the step of aligning comprises extracting certain features from the first image and the second image, and registering the features.

8. The method according to claim 1 wherein the step of aligning comprises using common radiotherapy patient setup protocols.

9. The method according to claim 1 wherein the first and second images are sufficiently well aligned that explicit fusion is not necessary.

10. The method according to claim 1 wherein the first sinogram data set is obtained from megavoltage CT images and the second sinogram data set is obtained from kilovoltage CT images.

11. The method according to claim 1 wherein the first sinogram data set is obtained from CT images and the second sinogram data set is obtained from MRI images.

12. The method according to claim 1 further comprising the step of completing one or more iterations by substituting the third image for the first image.

13. The method according to claim 1 further comprising the steps of using the third image for any of the following: contouring, patient setup, patient repositioning, dose registration, dose calculation, dose patching, dose reconstruction, dose verification, delivery modification, plan selection, replanning, re-optimization, delivery verification, deformable patient registration, or deformable dose registration.

14. The method according to claim 1 wherein the first sinogram data set is obtained from a tomographic or volume-imaging modality.

15. The method according to claim 1 wherein the second sinogram data set is obtained from a tomographic or volume-imaging modality.

16. The method according to claim 1 wherein any of the sinograms or images are collected using fan-beam geometries.

17. The method according to claim 1 wherein any of the sinograms or images are collected using cone-beam geometries.

18. The method according to claim 1 wherein any of the sinograms or images are collected using helical geometries.

19. The method according to claim 1 wherein any of the sinograms or images are collected using planar image or data converted into tomographic-equivalent images or sinograms, or volume images.

20. The method according to claim 1 wherein the step of extracting data utilizes patient shape, patient size, patient anatomy, and patient density information.

21. The method according to claim 20 wherein the patient's shape, size, shape, anatomy, and density has changed between obtaining the first sinogram data set and the second sinogram data set.

22. A method of augmenting a tomographic projection image of a patient, the method comprising the steps of:
   obtaining a sinogram data set from a patient, the sinogram data set containing limited data;
   converting the limited data sinogram data set into a limited data image;
   obtaining a data image from the patient, the data image containing complete data;
   fusing the complete data image to the limited data image to obtain a transformed complete data image;
   reprojecting a complete sinogram data set from the transformed complete image;
   augmenting the limited data sinogram data set with additional data obtained from the reprojected complete sinogram data set that is missing from the limited data sinogram data set; and
   converting the augmented limited data sinogram data set into an augmented image without significant artifacts.

23. The method according to claim 22 wherein the step of fusing comprises extracting certain features from the limited data image and the complete data image, and registering the features into the transformed complete data image.

24. The method according to claim 22 wherein the step of fusing is performed manually.

25. The method according to claim 22 wherein the step of fusing is performed automatically.

26. The method according to claim 22 wherein the step of fusing is performed using geometric features, gradient methods or voxel-similarity techniques.

27. The method according to claim 22 wherein the limited data sinogram data set, the reprojected sinogram data set and the augmented limited data sinogram data set is represented by a data matrix, wherein each row represents a gantry position, a gantry angle, or a ray angle; and each column represents a detector number, a detector distance, a detector angle, or a ray position; and a third sinogram dimension may optionally represent multiple detector rows.

28. The method according to claim 27 further comprising the steps of comparing the data matrix of the reprojected sinogram data set to the data matrix for the limited data sinogram data set and determining what data is missing from the limited data sinogram data set.

29. The method according to claim 22 further comprising the steps of using the image converted from the limited data sinogram data set for any of the following: contouring, patient setup, patient repositioning, dose registration, dose calculation, dose patching, dose reconstruction, dose verification, delivery modification, plan selection, replanning, re-optimization, delivery verification, or deformable patient registration.

30. The method according to claim 22 wherein the initial limited data sinogram data set is converted to an artifact-prone image.

31. A method of augmenting a tomographic projection image of a patient, the method comprising the steps of:
  obtaining a first sinogram data set from a patient, the first sinogram data set containing limited data;
  reconstructing the first sinogram data set into a first image;
  obtaining a second image from a patient, the second image containing complete data;
  fusing the second image to the first image to obtain an aligned image, so that optimal registration between the first and second image is obtained;
  reprojecting the aligned image into a reprojected sinogram data set;
  extracting data from the reprojected sinogram data set that is not available in the first sinogram data set;
  augmenting the first sinogram data set with the extracted data from the reprojected sinogram data set to obtain an augmented sinogram data set; and
  reconstructing the augmented sinogram data set into a third image.

32. A method of reconstructing a limited data image from a complete data image, the method comprising the steps of:
  obtaining a first sinogram data set from a patient, the first sinogram data set containing limited data;
  reconstructing the first sinogram data set into a first image;
  obtaining a second image from the patient, the second image containing complete data;
  fusing the first image to the second image;
  realigning the second image to the first image to obtain an aligned image;
  reprojecting the aligned image into a reprojected sinogram data set;
  augmenting the first sinogram data set with data extracted from the reprojected sinogram data set that is not available in the first sinogram data set to obtain an augmented sinogram data set; and
  reconstructing the augmented sinogram data set into an aligned-reprojection image.

33. A method of creating an aligned-reprojection image of a patient undergoing radiotherapy from a limited data image and a complete planning data image, the method comprising the steps of:
  obtaining a complete planning sinogram data set from a patient representing the treatment area of the patient;
  reconstructing the complete planning sinogram data set into a complete planning image;
  obtaining a limited sinogram data set from a patient representing the treatment area of the patient;
  reconstructing the limited sinogram data set into a limited image;
  aligning the complete planning image to the limited image to obtain an aligned image;
  reprojecting the aligned image into a reprojected sinogram data set;
  comparing the reprojected sinogram data set to the limited sinogram data set;
  extracting data from the reprojected sinogram data set that is not available in the limited sinogram data set;
  augmenting the limited sinogram data set by adding the extracted data from the reprojected sinogram data set to obtain an augmented sinogram data set;
  reconstructing the augmented sinogram data set into an aligned-reprojection image; and
  aligning the aligned-reprojection image to the limited image to obtain a re-aligned image.

* * * * *